(12) United States Patent　　　　　　　　(10) Patent No.: US 8,951,258 B2
Peultier et al.　　　　　　　　　　　　　　　(45) Date of Patent: Feb. 10, 2015

(54) SPINAL CORRECTION SYSTEM AND METHOD

(71) Applicant: Warsaw Orthopedic, Inc., Warsaw, IN (US)

(72) Inventors: Bertrand Peultier, Les Hospitaux Neufs (FR); Loic Josse, Yens (CH); Jean Charles LeHuec, Pessac (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 8 days.

(21) Appl. No.: 13/782,450

(22) Filed: Mar. 1, 2013

(65) Prior Publication Data

US 2014/0249591 A1　　Sep. 4, 2014

(51) Int. Cl.
　　*A61B 17/70*　　　(2006.01)
　　*A61B 17/88*　　　(2006.01)
(52) U.S. Cl.
　　CPC ............ *A61B 17/8866* (2013.01); *A61B 17/88* (2013.01)
　　USPC ........................................ 606/86 A; 606/279
(58) Field of Classification Search
　　USPC .................. 606/246, 279, 86 A, 102, 105, 90
　　See application file for complete search history.

(56) References Cited

U.S. PATENT DOCUMENTS

| | | | |
|---|---|---|---|
| 4,271,836 A | 6/1981 | Bacal et al. | |
| 4,422,451 A | 12/1983 | Kalamchi | |
| 5,020,519 A | 6/1991 | Hayes et al. | |
| 5,704,937 A | 1/1998 | Martin | |
| 5,966,827 A | 10/1999 | Horvath et al. | |
| 6,551,316 B1 | 4/2003 | Rinner et al. | |
| 6,716,218 B2 | 4/2004 | Holmes et al. | |
| 6,739,068 B1 | 5/2004 | Rinner | |
| D566,271 S | 4/2008 | Gao et al. | |
| 7,454,939 B2 | 11/2008 | Garner et al. | |
| 7,922,750 B2 | 4/2011 | Trautwein et al. | |
| 8,157,809 B2 | 4/2012 | Butters et al. | |
| 2003/0205075 A1 | 11/2003 | Strippgen et al. | |
| 2004/0176775 A1 | 9/2004 | Burkus et al. | |
| 2005/0021040 A1 | 1/2005 | Bertagnoli | |
| 2006/0111712 A1 | 5/2006 | Jackson | |
| 2007/0233143 A1 | 10/2007 | Josse et al. | |
| 2008/0119862 A1 | 5/2008 | Wicker et al. | |
| 2009/0005784 A1 | 1/2009 | Blain et al. | |
| 2009/0228051 A1 | 9/2009 | Kolb et al. | |
| 2009/0281582 A1 | 11/2009 | Villa et al. | |
| 2010/0021385 A1 | 1/2010 | Kudo et al. | |
| 2010/0262198 A1 | 10/2010 | Braunschweiler et al. | |
| 2012/0043269 A1 | 2/2012 | Shariff et al. | |

*Primary Examiner* — Pedro Philogene
*Assistant Examiner* — David Comstock

(57) ABSTRACT

A surgical instrument comprises a first arm extending between a first end and a second end including a first pivot engageable with a first spinal construct disposed with a first vertebral surface. A second arm is connected with the first arm via a second pivot. The second arm extends between a first end and a second end including a third pivot engageable with a second spinal construct disposed with a second vertebral surface. The arms are relatively movable to rotate the first spinal construct relative to the first pivot and the second spinal construct relative to the third pivot such that the first vertebral surface is moved relative to the second vertebral surface. Systems and methods of use are disclosed.

20 Claims, 10 Drawing Sheets

SPINAL CORRECTION SYSTEM AND METHOD

TECHNICAL FIELD

The present disclosure generally relates to medical devices for the treatment of spinal disorders, and more particularly to a surgical system and method for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. Correction treatments used for positioning and alignment may employ implants, such as, for example, spinal constructs and interbody devices, for stabilization of a treated section of a spine. This disclosure describes an improvement over these prior art technologies.

SUMMARY

Accordingly, in one embodiment, in accordance with the principles of the present disclosure, a surgical instrument is provided. The surgical instrument comprises a first arm extending between a first end and a second end including a first pivot engageable with a first spinal construct disposed with a first vertebral surface. A second arm is connected with the first arm via a second pivot. The second arm extends between a first end and a second end including a third pivot engageable with a second spinal construct disposed with a second vertebral surface. The arms are relatively movable to rotate the first spinal construct relative to the first pivot and the second spinal construct relative to the third pivot such that the first vertebral surface is moved relative to the second vertebral surface.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
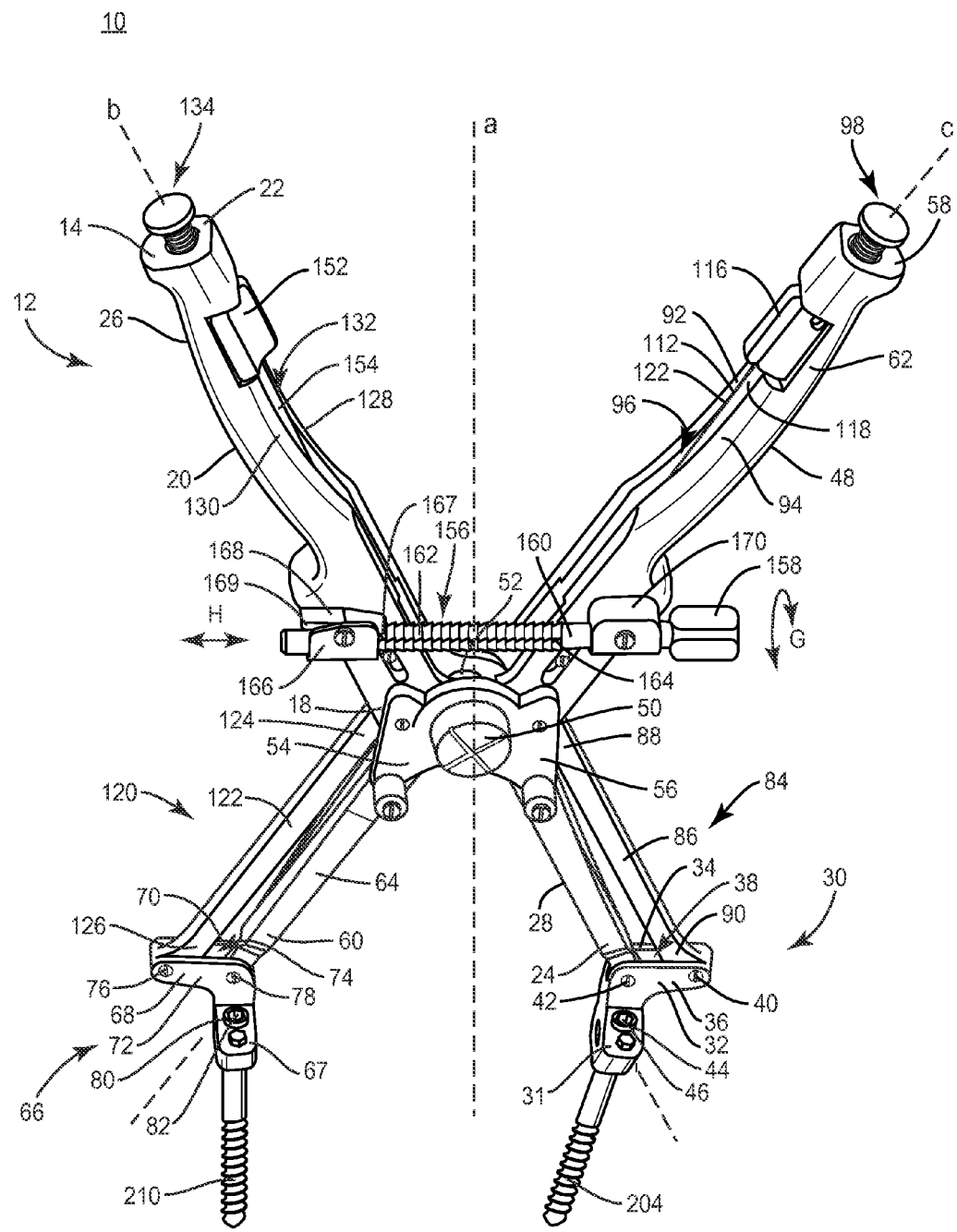
FIG. 1 is a perspective view of one embodiment of a spinal correction system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder.

In one embodiment, the system includes instruments and tools for correcting a sagittal deformity and rebalancing a spine of a body. In one embodiment, the present system is employed to treat degenerative deformities of a spine in a sagittal plane, for example, ankylosing spondylitis. It is envisioned that the system is employed to treat hyper-kyphosis, flat lumbar back and cervical hyper lordosis, including disorders that create an unbalance of a body and loss of alignment between body parts. In one embodiment, the system provides a selected amount of correction to apply a selected balance to a spine and provides control and adjustment to the amount of correction. In one embodiment, the system includes a series of tools and instruments that allow formulation of a type of correction applied and can control the correction stabilization using posterior instrumentation.

In one embodiment, the system includes an instrument that corrects the sagittal profile of a spine to balance a body by modifying curvatures of a spine with changes and correction to angles of lumbar and cervical lordosis and/or thoracic kyphosis. It is contemplated that angles for correcting lumbar lordosis include a range of 60 degrees+/−10 degrees. It is contemplated that angles for correcting lumbar lordosis include an angle approximately equal to an angle of pelvic incidence plus 10 degrees.

In one embodiment, the system includes a pelvic goniometer that allows measuring pelvic incidence of a body. In one embodiment, the goniometer indicates a sacral slope of a body corresponding to a measured pelvic incidence and a lumbar lordosis corresponding to the sacral slope. In one embodiment, the goniometer estimates normal lumbar lordosis based on statistical data.

In one embodiment, the system includes an instrument that applies correction and contours a spinal rod and forces a connection of the spinal rod to bone screws. In one embodiment, the system includes a reduction plier instrument that controls correction by driving an angular correction and provides indicia of initial and final angles of a curvature. In one embodiment, the plier instrument is rigidly connected to posterior pedicle screws to create a bridge over the portion of a spine to be corrected and maneuverable for correction. In one embodiment, the plier instrument provides a progressive correction such that the instrument is releasably lockable. In one embodiment, the instrument provides reversible correction such that the instrument can increase or reduce lordosis. In one embodiment, the instrument provides an indication of an amount of correction achieved and a securing mechanism to avoid an anterior collapse of an osteotomised vertebrae. In one embodiment, the instrument includes one or a plurality of adaptors to connect various screw systems. It is envisioned that the instrument can bridge together a multi axial screw (MAS) to shear a load on multiple vertebral levels.

In one embodiment, the instrument controls a correction angle of vertebrae and rotation of pedicle screws. In one embodiment, the instrument is placed in two positions, such as, for example, an initial state and a corrected state. In one embodiment, the instrument is rigidly connected to pedicle screws and the screws are driven from their posterior heads. In one embodiment, the pedicle screws rotate in a sagittal plane about a point disposed at an anterior end of the screw. In one embodiment, a distance between tips of the screws is substantially constant during correction motion to protect against collapse of the anterior spine. In one embodiment, the instrument controls an angle of rotation of the pedicle screws and indicates an angle between the pedicle screws and an amount of closure angle. In one embodiment, the instrument includes arms having a linkage disposed in a parallelogram configuration. In one embodiment, the instrument disposes screws at an initial angle with an adjustment linkage. It is envisioned that the pliers are movable to rotate screws to a final angle, which includes the initial angle plus a closure angle.

In one embodiment, the instrument facilitates permanently implanting spinal rods according to the contour of the spine in a sagittal plane of a body. In one embodiment, the instrument evaluates an angle between screws to contour a template rod.

In one embodiment, a method is provided for contouring a spinal rod, the method comprising the steps of: connecting a reduction plier instrument to a spine; introducing a sample of a straight rod template; connecting the template to the instrument; maneuvering the instrument to correct the spine, which automatically contours the template to the proper shape; disconnecting the template from the instrument; and duplicating the contouring of the template on an implantable spinal rod. In one embodiment, the instrument includes a three point rod bender for shaping the implantable spinal rod. In one embodiment, the system is employed with a pedicle subtraction osteotomy from a posterior approach affecting a lower lumbar at the L4, L3 or L2 vertebral levels.

In one embodiment, the method includes the instrument being adjusted to the spinal anatomy via a variable inter-pedicular distance and variable screw directions. It is envisioned that a correction is applied by securing an initial spinal size, for example, an initial height of an anterior spine and increasing local lordosis and maintaining the height of the anterior spine such that a correction rotation point is located anteriorly.

In one embodiment, the method adjusts an anatomy by adjusting to an inter-pedicular distance via opening and closing the instrument. In one embodiment, arms of the instrument are connected with a pivot hinge. In one embodiment, the instrument is adjusted to the pedicle screw direction by pressing and releasing an end push button. In one embodiment, tips of screws are pivot hinged to the arms. In one embodiment, parallelogram linkages are used to report an angle to a center of the instrument. In one embodiment, the parallelograms are free to deform during motion of the instrument. In one embodiment, a secondary mechanism is provided for ergonomic manipulation of angle.

In one embodiment, the instrument is secured to an initial configuration of screws via rotation of a lock button. In one embodiment, the instrument partially locks motion of the parallelogram linkages. In one embodiment, a parallelogram linkage is linked to an opposing arm at the center of the instrument. In one embodiment, the instrument includes ergonomic locking, such as, for example, locking buttons at the handles. In one embodiment, the instrument is closed to apply correction. It is envisioned that the arms are manipulated to increase a local lordosis angle. In one embodiment, the instrument maintains a height of the anterior spine. In one embodiment, motion of the instrument is the result of the parallelogram linkages being linked to opposing arms.

In one embodiment, the instrument includes a ratchet, which is provided to maintain the actual distraction/compression of the instrument and/or maintain opening or closing. In one embodiment, the instrument includes an angle indicator to indicate the amount of correction angle. In one embodiment, the angle is indicated on the ratchet. In one embodiment, the angle indicator displays the difference between the initial angle and the final angle corresponding to the amount of correction.

It is contemplated that one or all of the components of the system may be disposable, peel pack and/or pre packed sterile devices. One or all of the components of the system may be reusable. The system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, vessels, ligaments, tendons, cartilage and/or bone unless specifically referred to otherwise.

Figure 2:
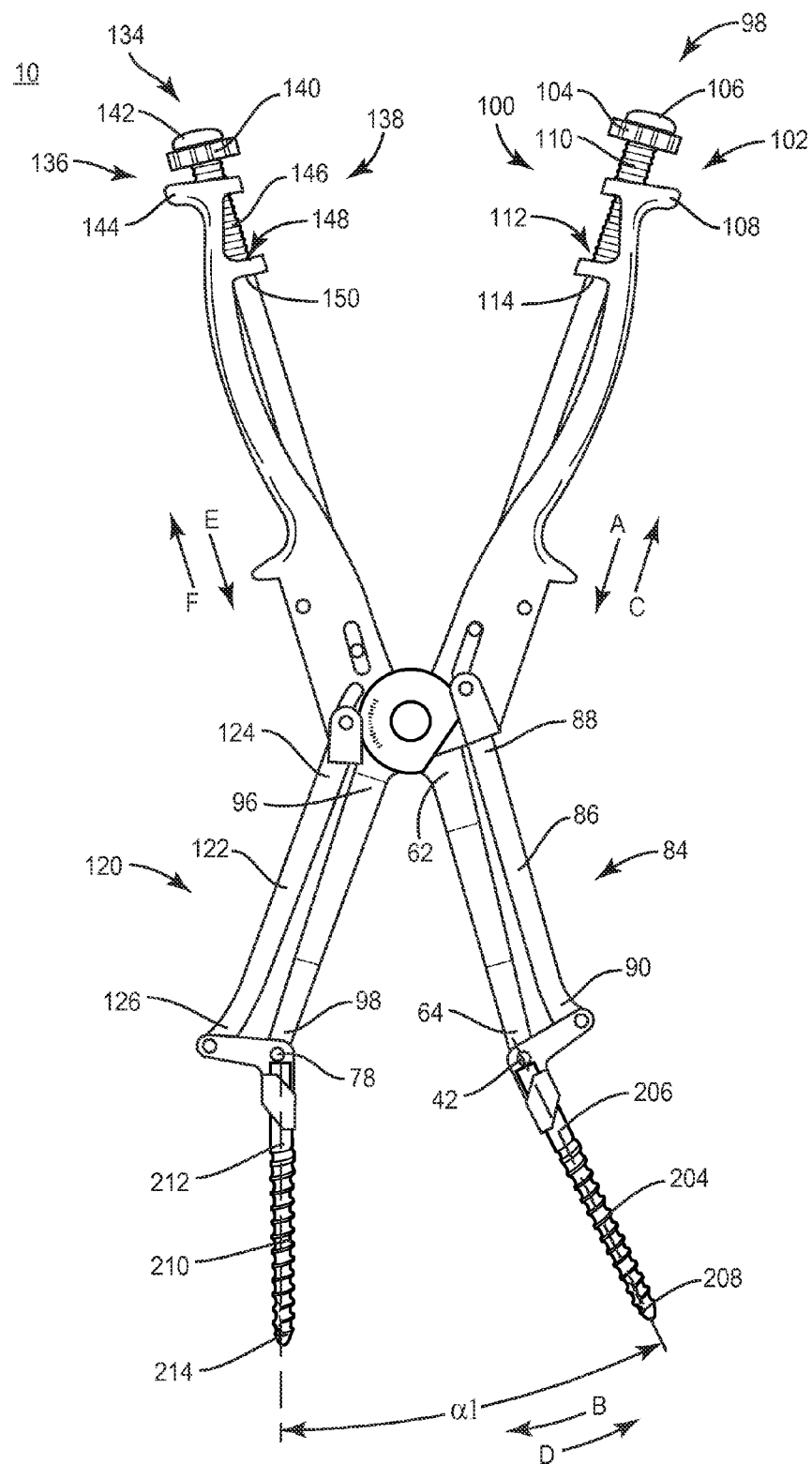
FIG. 2 is a plan view of the system shown in FIG. 1.
Figure 3:
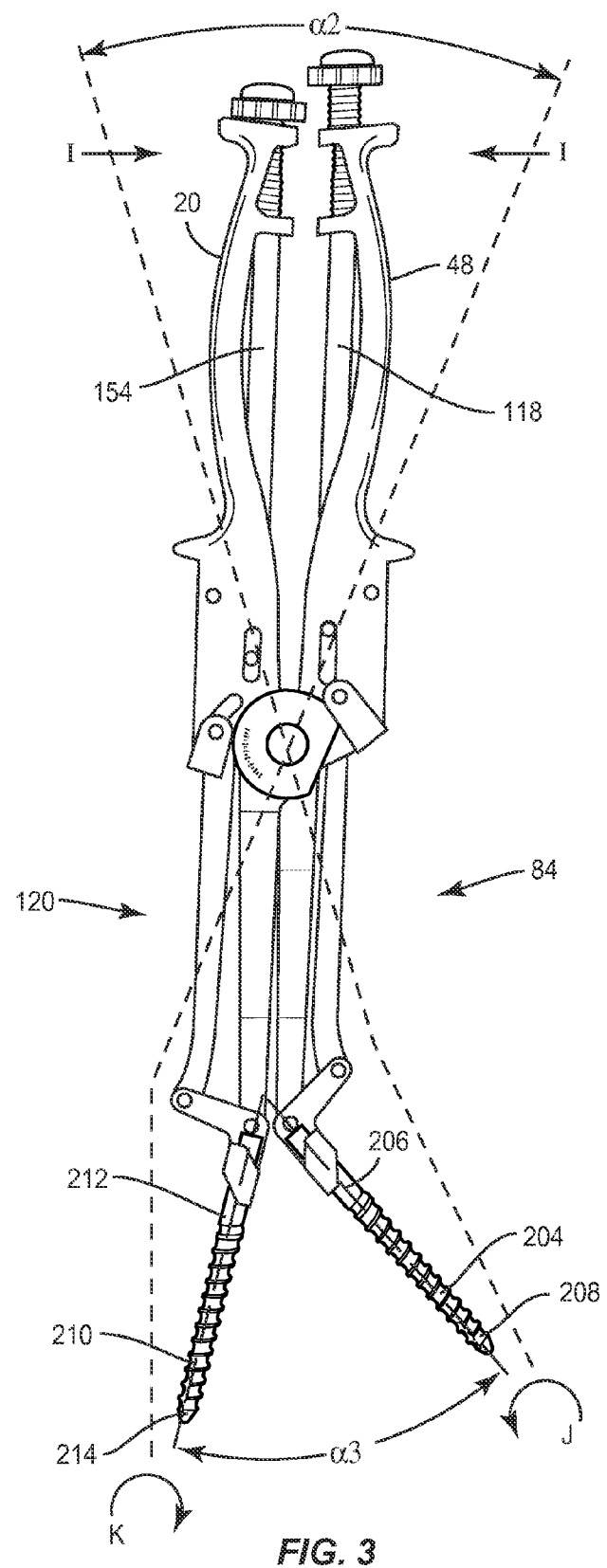
FIG. 3 is a plan view of the system shown in FIG. 1.

The following discussion includes a description of a system in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there is illustrated components of a system, such as, for example, a spinal correction system 10 in accordance with the principles of the present disclosure.

The components of system 10 can be fabricated from biologically acceptable materials suitable for medical applications, including metals, synthetic polymers, ceramics, bone material, tissue and/or their composites, depending on the particular application and/or preference of a medical practitioner. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes an instrument 12 configured for engagement with spinal constructs to correct a spinal disorder, such as, for example, a sagittal deformity, as described herein. Instrument 12 extends between a first portion 14 and a second portion 16. Instrument 12 defines a longitudinal axis a and an intermediate portion 18 is disposed between portions 14, 16.

Instrument 12 includes an arm 20 that extends between a first end 22 and a second end 24. It is contemplated that the cross section and/or overall configuration of arm 20 may be variously configured, such as, for example, round, oval, oblong, square, rectangular, polygonal, irregular, uniform, non-uniform, offset, staggered, tapered, consistent or variable, depending on the requirements of a particular application. It is further contemplated that arm 20 may include an outer gripping surface configured for gripping by a hand of a practitioner. It is envisioned that the gripping surface may be, such as, for example, rough, arcuate, undulating, mesh, porous, semi-porous, dimpled and/or textured according to the requirements of a particular application.

Arm 20 includes a member 26 disposed adjacent end 22 and a member 28 disposed adjacent end 24. Members 26, 28 are disposed in substantially linear alignment and define a longitudinal axis b. Member 26 is integrally connected or monolithically formed with member 28 such that members 26, 28 simultaneously rotate relative to a second arm and relative to axis a.

Member 28 includes an implant connector 30 that is configured for engagement with a spinal construct disposed with a vertebral surface, as described herein. Connector 30 includes an angled configuration to facilitate rotation of a spinal construct. Connector 30 includes a section 31 connected to and disposed in a substantially perpendicular orientation relative to a section 32. Connector 30 includes spaced apart walls 34 and 36 that define a cavity, such as, for example, a channel 38. Channel 38 is configured for disposal of member 28 and a linkage, described herein. Connector 30 is attached to member 28, and the linkage via a screw, post and/or pins 40, 42. It is envisioned that section 31 may be disposed in alternate orientations relative to section 32, such as, for example, transverse and/or other angular orientations such as acute or obtuse, co-axial and/or may be offset or staggered.

Connector 30 is movably connected to member 28 via a pivot, which includes pin 42 to facilitate pivotal movement of connector 30 and rotation thereof relative to axis b. Connector 30 includes an inner surface 44 that defines an opening 46. Opening 46 is configured for disposal of a proximal end of a bone fastener to facilitate rotation of a bone fastener relative to and about pin 42. In one embodiment, bone fastener attachment units 11 (FIG. 7) may be attached to opening 46 to facilitate engagement of various bone fastener types.

An arm 48 is connected to arm 20 via a pivot, which includes a hinge 50. Hinge 50 is centrally disposed adjacent portion 18 and configured to facilitate rotation of arm 20 relative to arm 48, and arms 20, 48 relative to axis a. It is contemplated that hinge 50 may be variously configured such as, for example, pin, post, screw, living hinge, ratchet and/or concentric parts. Hinge 50 includes a central post 52 that facilitates rotation of arms 20, 48 and pivotal movement and relative rotation therebetween. Hinge 50 includes rotatable plates 54 and 56 mounted to arms 20, 48 via post 52. Plate 54 is connected to arm 20 and a linkage and plate 56 is connected to arm 48 and a linkage, as described herein. Plates 54, 56 facilitate bending of a rod template, as described herein.

Arm 48 extends between a first end 58 and a second end 60. Arms 20 and 48 are configured for relative rotation and pivotal movement relative to axis a to move from a first configuration to a second configuration to correct a sagittal deformity, as described herein. It is contemplated that the cross section and/or overall configuration of arm 48 may be variously configured, such as, for example, round, oval, oblong, square, rectangular, polygonal, irregular, uniform, non-uniform, offset, staggered, tapered, consistent or variable, depending on the requirements of a particular application. It is further contemplated that arm 48 may include an outer gripping surface configured for gripping by a hand of a practitioner. It is envisioned that the gripping surface may be, such as, for example, those alternatives described herein.

Arm 48 includes a member 62 disposed adjacent end 58 and a member 64 disposed adjacent end 60. Members 62, 64 are disposed in substantially linear alignment and define a longitudinal axis c. Member 62 is integrally connected or monolithically formed with member 64 such that members 62, 64 simultaneously rotate relative to arm 20.

Member 64 includes an implant connector 66 that is configured for engagement with a spinal construct disposed with a vertebral surface, as described herein. Connector 66 includes an angled configuration to facilitate rotation of a spinal construct. Connector 66 includes a section 67 connected to and disposed in a substantially perpendicular orientation relative to a section 68. Connector 66 includes spaced apart walls 70 and 72 that define a cavity, such as, for example, a channel 74. Channel 74 is configured for disposal of member 64 and a linkage, as described herein. Connector 66 is attached to member 64, and the linkage via a screw, post and/or pins 76, 78. It is envisioned that section 67 may be disposed in alternate orientations relative to section 68, such as, for example, transverse and/or other angular orientations such as acute or obtuse, co-axial and/or may be offset or staggered.

Connector 66 is movably connected to member 64 via a pivot, which includes pin 78 to facilitate pivotal movement of connector 66 and rotation thereof relative to axis c. Connector 66 includes an inner surface 80 that defines an opening 82. Opening 82 is configured for disposal of a proximal end of a bone fastener to facilitate rotation of a bone fastener relative to and about pin 78. In one embodiment, bone fastener attachment units 11 (FIG. 7) may be attached to opening 82 to facilitate engagement of various bone fastener types.

Member 28 includes a linkage 84 disposed therealong and being configured for rotating a bone fastener disposed with connector 30, as described herein. Linkage 84 includes a link 86 that is disposed in substantially parallel relation relative to member 28. Link 86 extends between a first end 88 and a second end 90.

End 88 is connected to plate 56 adjacent hinge 50 and movable therewith, as described herein. End 90 is connected to section 32 to cause movement thereof and rotation of a bone fastener. An actuator causes movement of link 86, which rotates relative to the actuator, as described herein. Link 86 causes movement of section 32, which rotates relative to link 86. In turn, section 32 rotates section 31 of connector 30, which rotates a bone fastener relative to pin 42. Linkage 84 includes link 86, plate 56, member 28 and connector 30, which are disposed in a parallelogram configuration. This configuration facilitates selective rotation according to the parallelogram geometry.

Member 62 includes walls 92 and 94 that define a channel 96 configured for disposal of an actuator 98. Actuator 98 is connected to linkage 84 and is configured to selectively adjust rotation of the spinal construct, for example, to an initial orientation, as described herein. Actuator 98 includes a knob 102, as shown in FIG. 2. Knob 102 includes an outer surface 104 that defines a head 106. Head 106 is configured for a stop engagement with a ledge 108 defined by member 62 to define a first translation limit and a second translation limit of actuator 98. Surface 104 defines a threaded portion 110 that engages member 62 for translation of actuator 98.

A passageway 112 is disposed within member 62. Passageway 112 includes an inner threaded surface 114. Surface 114 and portion 110 are configured for threaded engagement during axial translation. Actuator 98 includes a lock 100 that defines a tab 116. Tab 116 is engageable to selectively and releasably lock connector 30 and a spinal construct attached therewith in a selected orientation.

Actuator 98 includes a link 118 configured for axial translation and engagement with link 86 of linkage 84, as shown in FIG. 3. Knob 102 is rotatable in a clockwise direction such that portion 110 and surface 114 engage to translate link 118 in an axial direction, as shown by arrow A in FIG. 2. Link 118 engages link 86 causing connector 30 and the spinal construct to rotate relative to pin 42, as described herein, in a direction as shown by arrow B.

Knob 102 is rotatable in a counterclockwise direction such that portion 110 and surface 114 engage to translate link 118 in an axial direction, as shown by arrow C. Link 118 engages link 86 of linkage 84 causing connector 30 and the spinal construct to rotate relative to pin 42, as described herein, in a direction as shown by arrow D. It is contemplated that link 118 and link 86 may be connected for engagement via a pivot, hinge, pin threaded engagement, male/female engagement and/or overlapping linkage.

Member 64 includes a linkage 120 disposed therealong and being configured for rotating a bone fastener disposed with connector 66, as described herein. Linkage 120 includes a link 122 that is disposed in substantially parallel relation relative to member 64. Link 122 extends between a first end 124 and a second end 126.

End 124 is connected to plate 54 adjacent hinge 50 and movable therewith, as described herein. End 126 is connected to section 68 to cause movement thereof and rotation of a bone fastener. An actuator causes movement of link 122, which rotates relative to the actuator, as described herein. Link 122 causes movement of section 68, which rotates relative to link 122. In turn, section 68 rotates section 67 of connector 66, which rotates a bone fastener relative to pin 78. Linkage 120 includes link 122, plate 54, member 64 and connector 66, which are disposed in a parallelogram configuration. This configuration facilitates selective rotation according to the parallelogram geometry.

Member 26 includes walls 128 and 130 that define a channel 132 configured for disposal of an actuator 134. Actuator 134 is connected to linkage 120 and is configured to selectively adjust rotation of the spinal construct, for example, to an initial orientation, as described herein. Actuator 134 includes a knob 138, as shown in FIG. 2. Knob 138 includes an outer surface 140 that defines a head 142. Head 142 is configured for a stop engagement with a ledge 144 defined by member 26 to define a first translation limit and a second translation limit of actuator 134. Surface 140 defines a threaded portion 146 that engages member 26 for translation of actuator 134.

A passageway 148 is disposed within member 26. Passageway 148 includes an inner threaded surface 150. Surface 150 and portion 146 are configured for threaded engagement during axial translation. Actuator 134 includes a lock 136 that defines a tab 152. Tab 152 is engageable to selectively and releasably lock connector 66 and a spinal construct attached therewith in a selected orientation.

Actuator 134 includes a link 154 configured for axial translation and engagement with a link 122 of linkage 120, as shown in FIG. 3. Knob 138 is rotatable in a clockwise direction such that portion 146 and surface 150 engage to translate link 154 in an axial direction, as shown by arrow E in FIG. 2. Link 154 engages link 122 causing connector 66 and the spinal construct to rotate relative to pin 78, as described herein, in a direction as shown by arrow D.

Knob 138 is rotatable in a counter clockwise direction such that portion 146 and surface 150 engage to translate link 154 in an axial direction, as shown by arrow F. Link 154 engages link 122 of linkage 120 causing connector 66 and the spinal construct to rotate relative to pin 78, as described herein, in a direction as shown by arrow B. It is contemplated that link 154 and link 122 may be connected for engagement via a pivot, hinge, pin, threaded engagement, male/female engagement and/or overlapping linkage.

Instrument 12 includes a ratchet configured to maintain arms 20, 48 in a selected opening orientation, such as, for example, a selected distraction position and/or a selected closing orientation, such as, for example, a selected compression position of instrument 12. The ratchet includes a toothed rack 156 disposed adjacent portion 18, which is configured for bi-directional locking of arms 20, 48. Rack 156 is disposed transverse relative to instrument 12 and extends between a proximal portion, such as, for example, head 158 and a distal portion, such as, for example, shaft 160.

Shaft 160 defines a tooth surface 162 that includes gear teeth oriented in a first direction and a tooth surface 164 that includes gear teeth oriented in a second direction. Tooth surface 162 maintains arms 20, 48 in a selected opening orientation and tooth surface 164 maintains arms 20, 48 in a selected closing orientation, as described herein. Shaft 160 is rotatable, in the direction shown by arrows G in FIG. 1, via manipulation of head 158 to orient a particular tooth surface of shaft 160 into position for locking shaft 160 such that shaft 160 is translatable, in the direction shown by arrows H, in a first axial direction and prevented from translation in a second, opposing axial direction to maintain arms 20, 48 in a selected orientation.

A block 166 is mounted to arm 20 adjacent portion 18. Block 166 defines a passageway configured for slidable disposal and support of shaft 160. Block 166 includes a pivoting lever 168 that engages a particular tooth surface of shaft 160 to releasably fix arms 20, 48 in a selected orientation. Lever 168 includes a gear tooth 167 configured to engage tooth surface 162 to maintain arms 20, 48 in a selected opening orientation. Shaft 160 is rotatable into a position such that gear tooth 167 engages tooth surface 162 and allows slidable translation of shaft 160 relative to block 166 as members 28, 64 are expanded and spaced apart, for example, to distract vertebrae to a selected opening orientation. At a selected opening orientation, gear tooth 167 engages tooth surface 162 to fix the relative position of members 28, 64 and prevent contraction and closing of members 28, 64.

Lever 168 includes a gear tooth 169 configured to engage tooth surface 164 to maintain arms 20, 48 in a selected closing orientation. Shaft 160 is rotatable into a position such that gear tooth 169 engages tooth surface 164 and allows slidable translation of shaft 160 relative to block 166 as members 28, 64 are contracted and disposed in close proximity, for example, to compress vertebrae to a selected closing orientation. At a selected closing orientation, gear tooth 169 engages tooth surface 164 to fix the relative position of members 28, 64 and prevent expansion and opening of members 28, 64.

It is contemplated that block 166 may be fixed to arm 20 via a screw, snap, clip and/or adhesive. In one embodiment, block 166 is monolithically formed with arm 20. A block 170 is mounted to arm 48 adjacent portion 18. Block 170 defines a passageway configured for slidable disposal and support of shaft 160. It is contemplated that block 170 may be fixed to arm 48 via those alternative described herein. In one embodiment, block 170 is monolithically formed with arm 48.

Figure 6:
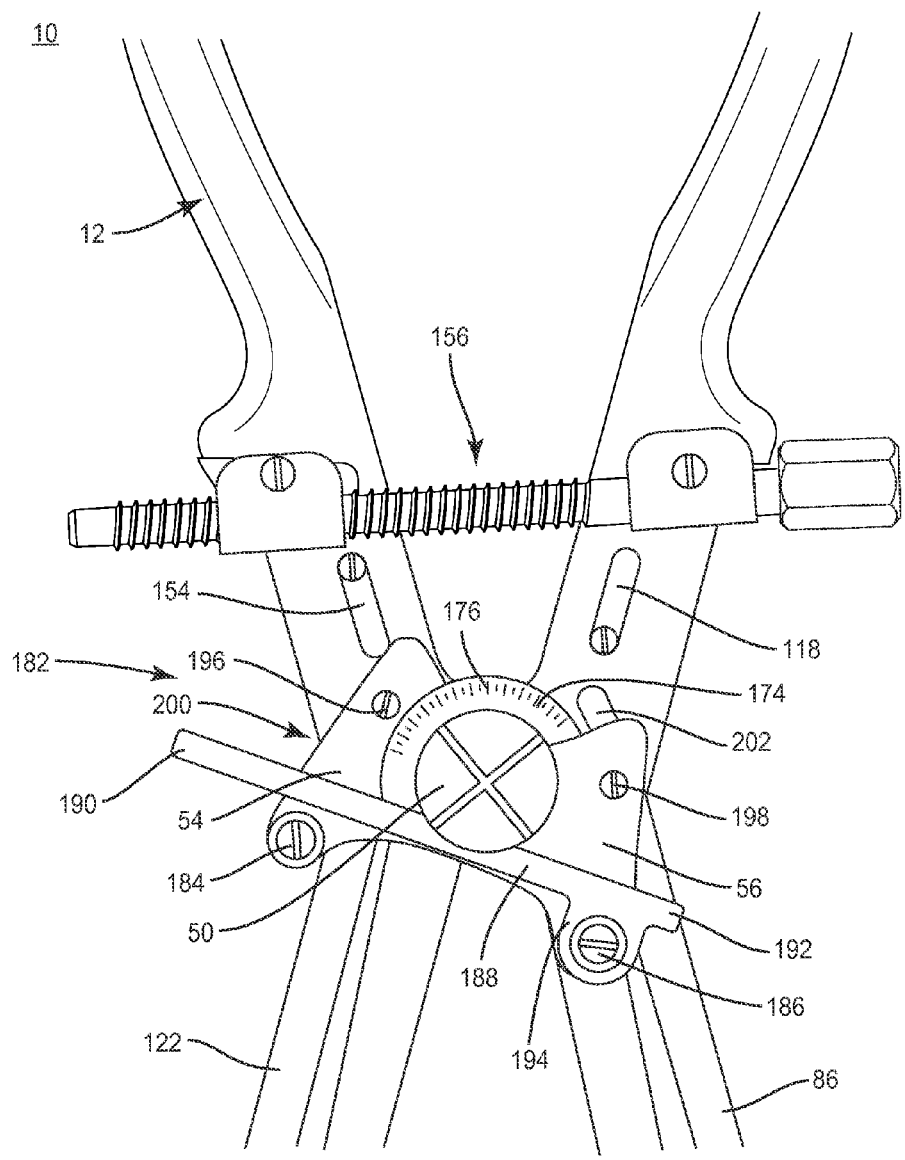
FIG. 6 is an enlarged break away view of one embodiment of components of the system shown in FIG. 1.

In one embodiment, as shown in FIG. 6, system 10, described above with regard to FIGS. 1-3, comprises instrument 12, which includes visual indicia, such as, for example, an angle indicator 174 formed with plate 56. Indicator 174 is disposed circumferentially about plate 56 configured to measure an angle between the spinal constructs attached to connectors 30 and 66 respectively. As arms 20, 48 are manipulated to correct a sagittal deformity, indicator 174 includes graduations 176 that comprise a plurality of spaced apart markings that represent and display a measured angular orientation of the spinal constructs. It is contemplated that indicator 174 may include an analog, such as, for example, a dial with a numerical indicator of angle and/or digital display, such as, for example, LED and/or LCD. It is further contemplated that the graduations may represent various indicia, such as, for example, numerical, alphabetic and/or specific conditions/orientations, such as, initial angle, closure angle, final angle and/or correction angle. In one embodiment, indicator 174 provides angle or other information used to measure a contour for an implantable spinal rod to be fastened with associated vertebral tissue.

In one embodiment, as shown in FIG. 6, system 10, described above with regard to FIGS. 1-3, comprises instrument 12, which includes a spinal rod bender 182. Bender 182 is configured to contour a spinal rod template according to an angle between spinal constructs attached to connectors 30 and 66, and an angle between pedicle screws relative to rotation of linkages 84, 120, and/or other parameters. In one embodiment, the contoured spinal rod template is employed to configure an implantable spinal rod (not shown) to be fastened with associated vertebral tissue. In one embodiment, indicator 174 and bender 182 are monolithically formed.

Bender 182 is disposed adjacent portion 18 and formed with hinge 50 and plates 54, 56, described above. Plate 54 is attached to link 122 via a pin 196 and plate 56 is attached to link 86 via a pin 198. Pin 196 slidably translates along a slot 200 defined by an outer surface of link 122 as link 122 engages link 154. Pin 198 slidably translates along a slot 202 defined by an outer surface of link 86 as link 86 engages link 118.

Plate 54 includes a post 184 and plate 56 includes a post 186. Hinge 50 and posts 184, 186 are configured for support and engagement with a spinal rod template 188 to be contoured according to the orientation of the spinal constructs and/or pedicle fasteners. Upon correction of a sagittal deformity of vertebrae, the vertebrae can be stabilized by implantation of implantable spinal rods. The implantable spinal rods are configured to the corrected shape of the vertebrae in a sagittal plane. Template 188 is disposed with bender 182, as described, and extends between a first end 190 and a second end 192. End 192 includes an opening 194 configured for releasable fixation with post 186 to position template 188 during contour. In one embodiment, as instrument 12 is manipulated to correct the sagittal deformity, template 188 is automatically contoured to the corrected configuration. Template 188 is removed from bender 182 and an implantable spinal rod can be contoured according to the configuration of template 188.

Figure 7:
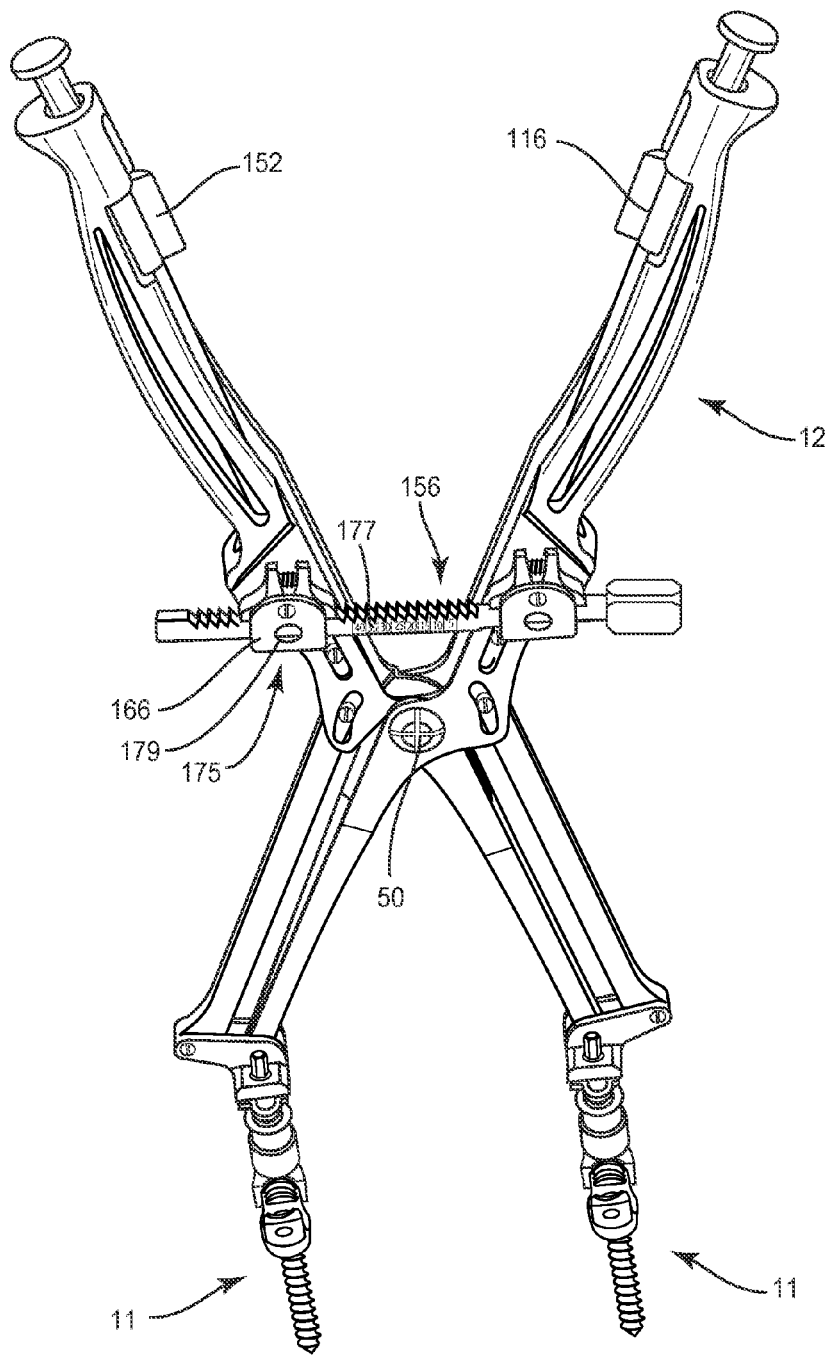
FIG. 7 is perspective view of one embodiment of the system shown in FIG. 1.

In one embodiment, as shown in FIG. 7, system 10, described above with regard to FIG. 6, comprises instrument 12, which includes visual indicia, such as, for example, an angle indicator 175, similar to indicator 174 described above, formed with rack 156, described above with regard to FIGS. 1-3. As arms 20, 48 are manipulated to correct a sagittal deformity, indicator 175 includes numerical graduations 177 disposed axially along rack 156, which are configured to represent and display a measured angle between the spinal constructs attached to connectors 30 and 66 respectively. Graduations 177 comprise a plurality of spaced apart markings used to measure and display an angular orientation of the spinal constructs. Block 166 defines an opening, such as, for example, a window 179 that facilitates representation and display of the measured angle between the spinal constructs.

System 10 includes a spinal construct, such as, for example, a bone fastener 204 configured for rotation relative to pin 42. Bone fastener 204 includes a posterior end, such as, for example, a head 206 configured for attachment with connector 30, and an anterior end, such as, for example, an elongated shaft 208 configured for penetrating tissue. Shaft 208 has a cylindrical cross section configuration and includes an outer surface having an external thread form. It is contemplated that the thread form may include a single thread turn or a plurality of discrete threads. It is further contemplated that other engaging structures may be disposed on shaft 208, such as, for example, a nail configuration, barbs, expanding elements, raised elements and/or spikes to facilitate engagement of shaft 208 with tissue, such as, for example, vertebrae.

It is envisioned that all or only a portion of shaft 208 may have alternate cross section configurations, such as, for example, oval, oblong, triangular, square, polygonal, irregular, uniform, non-uniform, offset, staggered, undulating, arcuate, variable and/or tapered. It is contemplated that the outer surface may include one or a plurality of openings. It is contemplated that all or only a portion of the outer surface may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 208 may be disposed at alternate orientations, relative to a longitudinal axis of bone fastener 204, such as, for example, transverse, perpendicular and/or other angular orientations such as acute or obtuse, co-axial and/or may be offset or staggered. It is further envisioned that all or only a portion of shaft 208 may be cannulated.

It is contemplated that shaft 208 may be made for attachment to bone, such as cervical, thoracic, lumbar and or sacral vertebral bone structures, or other tissues. In one embodiment, shaft 208 may be a screw, or could also be alternatively configured, for example, as a vertebral hook or clamp. It is contemplated that the threads may be self-tapping or intermittent, or may have more than one crest winding about shaft 208. In one embodiment, the outer surface may include an opening for accommodating a tool (not shown) for gripping or turning bone fastener 204.

System 10 includes a spinal construct, such as, for example, a bone fastener 210, similar to bone fastener 204 described above, configured for rotation relative to pin 78. Bone fastener 210 includes a head 212 configured for fixation with connector 66 and an elongated shaft 214 configured for penetrating tissue.

In operation, instrument 12 is manipulated for engagement with fasteners 204, 210 such that arms 20 and 48 are movable from a first configuration, as shown in FIG. 2, which may include fasteners 204, 210 being disposed at an initial angle and a second configuration, as shown in FIG. 3, which may include fasteners 204, 210 being disposed at a final corrected angle that may include the initial angle and a closure angle.

In the first configuration, arms 20, 48 are spaced apart and attached to bone fasteners 204, 210 such that head 206 is disposed with opening 46 and head 212 is disposed with opening 82. To selectively adjust orientation of shaft 208 relative to pin 42 for penetration with tissue, knob 102 is rotatable in a clockwise direction to translate link 118 in the direction shown by arrow A in FIG. 2 causing connector 30 and fastener 204 to rotate relative to pin 42, as described herein, in the direction shown by arrow B. Knob 102 is rotatable in a counter clockwise direction to translate link 118 in the direction shown by arrow C causing connector 30 and fastener 204 to rotate relative to pin 42, as described herein, in the direction shown by arrow D.

To selectively adjust orientation of shaft 214 relative to pin 78 for penetration with tissue, knob 138 is rotatable in a clockwise direction to translate link 154 in the direction shown by arrow E causing connector 66 and fastener 210 to rotate relative to pin 78, as described herein, in the direction shown by arrow D. Knob 138 is rotatable in a counter clockwise direction to translate link 154 in the direction shown by arrow F causing connector 66 and fastener 210 to rotate relative to pin 78, as described herein, in the direction shown by arrow B.

Actuators 98, 134 cause linkages 84, 120, respectively, to orient fastener 204 relative to fastener 210 at a first angular orientation, such as, for example, an initial angle $\alpha 1$ such that shafts 208, 214 are disposed to penetrate tissue at a selected angle according to the requirements of a particular application. The initial angle $\alpha 1$ is lockable via locks 100, 136, described above.

Fasteners 204, 210 are rotatable to the second configuration such that arms 20, 48 rotate fasteners 204, 210 for an angular correction of vertebrae in a sagittal plane of a body. Arms 20, 48 are drawn in adjacent relation and into close proximity, as shown by arrows I in FIG. 3, to rotate fastener 204 relative to fastener 210 through a closure angle $\alpha 1$ in the sagittal plane. Fastener 204 is rotated, in the direction shown by arrow J, relative to the pivot associated with pin 42. Fastener 204 is also rotated relative to a distal tip thereof disposed with tissue to facilitate angular correction. Fastener 210 is rotated, in the direction shown by arrow K, relative to the pivot associated with pin 78. Fastener 210 is also rotated relative to a distal tip thereof disposed with tissue to facilitate angular correction. In one embodiment, fasteners 204, 210 are disposed at a final angle $\alpha 3$, which includes angle $\alpha 1$ and angle $\alpha 2$. Final angle $\alpha 3$ is lockable via rack 156 described above.

In one embodiment, the distance between the tips of fasteners 204, 210 is maintained substantially constant during rotation through the closure angle to prevent anterior spine collapse. It is envisioned that angles $\alpha 1$, $\alpha 2$, $\alpha 3$ may be measured and displayed via the angle indicators and/or a spinal rod template may be disposed with a rod bender, as described above with regard to FIGS. 6 and 7.

In assembly, operation and use, as shown in FIGS. 1-8, system 10, similar to that described herein, is employed with a surgical procedure, such as, for example, a correction treatment to treat adolescent idiopathic scoliosis and/or Scheuermann's kyphosis of a spine. It is contemplated that one or all of the components of system 10 can be delivered or implanted as a pre assembled device or can be assembled in situ. System 10 may be completely or partially revised, removed or replaced.

For example, system 10 can be employed with a surgical correction treatment of an applicable condition or injury of an affected section of a spinal column and adjacent areas within a body, such as, for example, vertebrae V. It is envisioned that system 10 may be employed with one or a plurality of vertebra.

Figure 8:
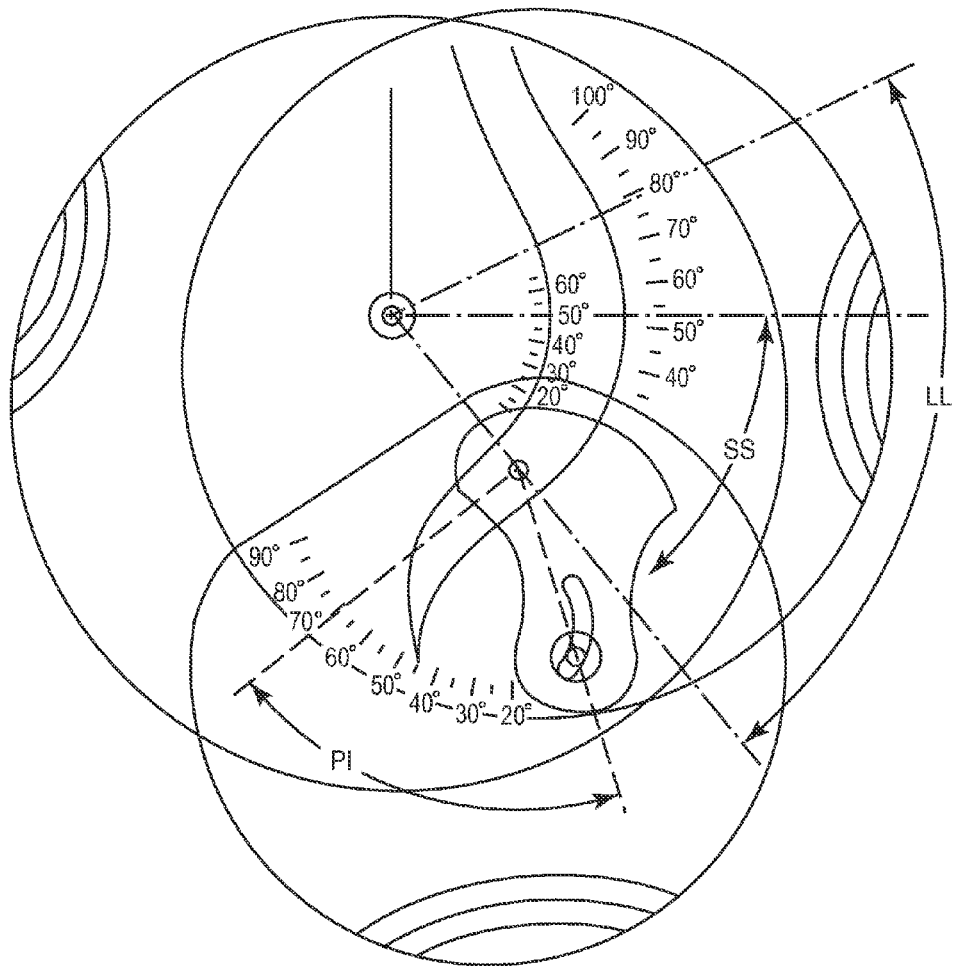
FIG. 8 is a schematic view of one embodiment of anatomical angles in accordance with the principles of the present disclose.

In one embodiment, to treat a selected section of vertebrae V, a pelvic goniometer (not shown) is employed that is configured for measuring the pelvic incidence on medical imaging, such as, for example, identification under x-ray, fluoroscopy, CT or other imaging techniques, as shown in FIG. 8. The goniometer can be employed to represent and display anatomical angle such as sacral slope (SS) corresponding to the measured pelvic incidence (PI) and the lumbar lordosis (LL) corresponding to the sacral slope. The goniometer measures a patient's parameter pelvic incidence on a standard X-ray. In one embodiment, the goniometer estimates the normal lumbar lordosis based on statistical data.

A medical practitioner obtains access to a surgical site including vertebrae V1, V2, V3 in any appropriate manner, such as through incision and retraction of tissues. It is envisioned that system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of the patient and a cutting instrument (not shown) creates a surgical pathway for implantation of components of system 10. A preparation instrument (not shown) can be employed to prepare tissue surfaces of vertebrae V, as well as for aspiration and irrigation of a surgical region according to the requirements of a particular surgical application.

Pilot holes or the like are made in selected vertebra V1 and V2 of vertebrae V for receiving bone fasteners 204, 210. An instrument is disposed adjacent vertebrae V at a surgical site and is manipulated to drive, torque, insert or otherwise connect bone fasteners 204, 210 to vertebrae V1 and V2, according to the particular requirements of the surgical treatment. Vertebra V3 is osteotomised according to the particular procedure.

Figure 4:
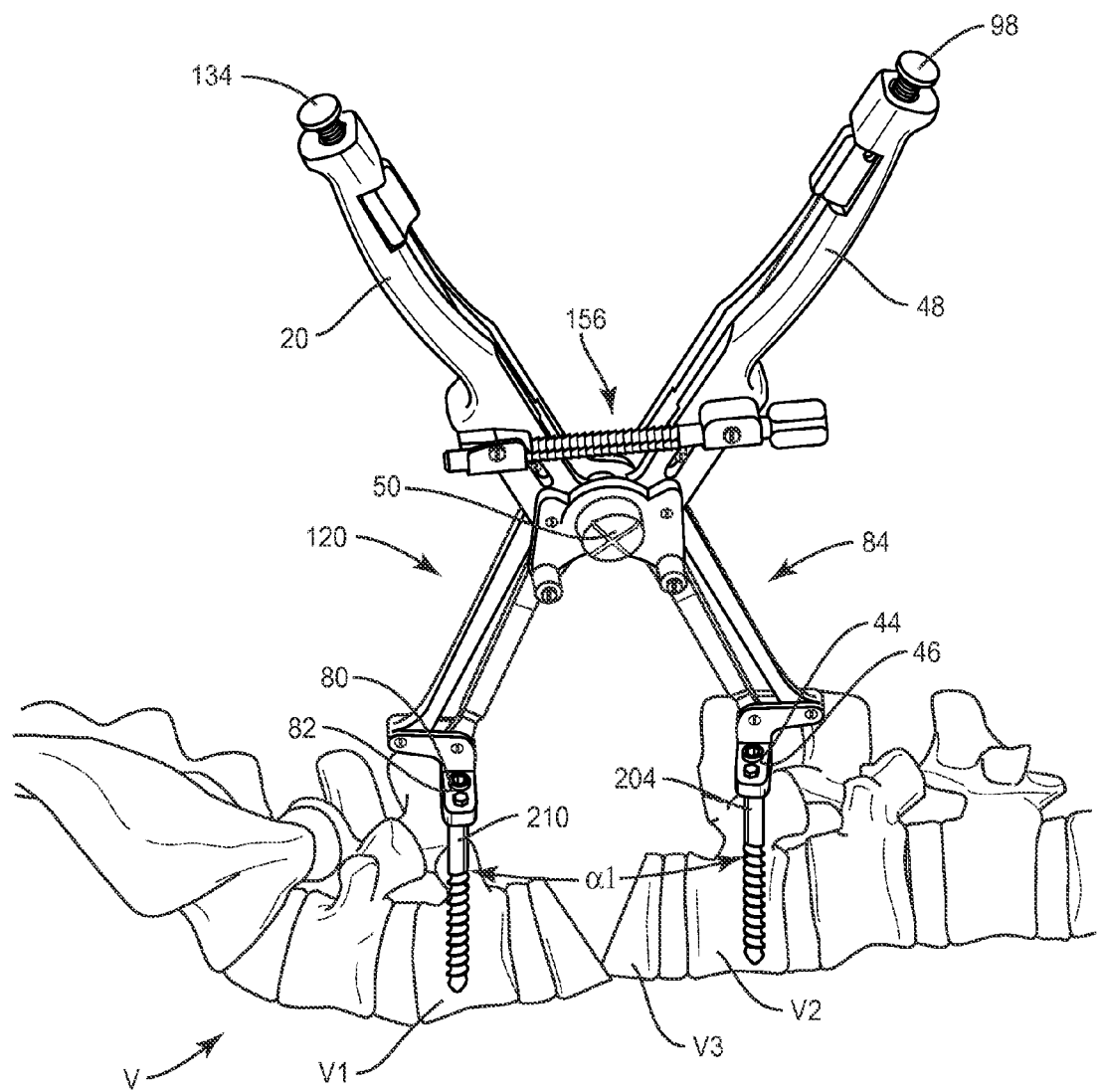
FIG. 4 is a perspective view of the system shown in FIG. 1 disposed with vertebrae.

Instrument 12 is disposed adjacent the surgical site and manipulated for engagement with fasteners 204, 210 such that arms 20 and 48 are movable from a first configuration, as shown in FIGS. 2 and 4. In the first configuration, arms 20, 48 are spaced apart and attached to bone fasteners 204, 210 such that head 206 is disposed with opening 46 and head 212 is disposed with opening 82. Shaft 208 is fixed with vertebra V2 and shaft 214 is fixed with vertebra V1.

Figure 5:
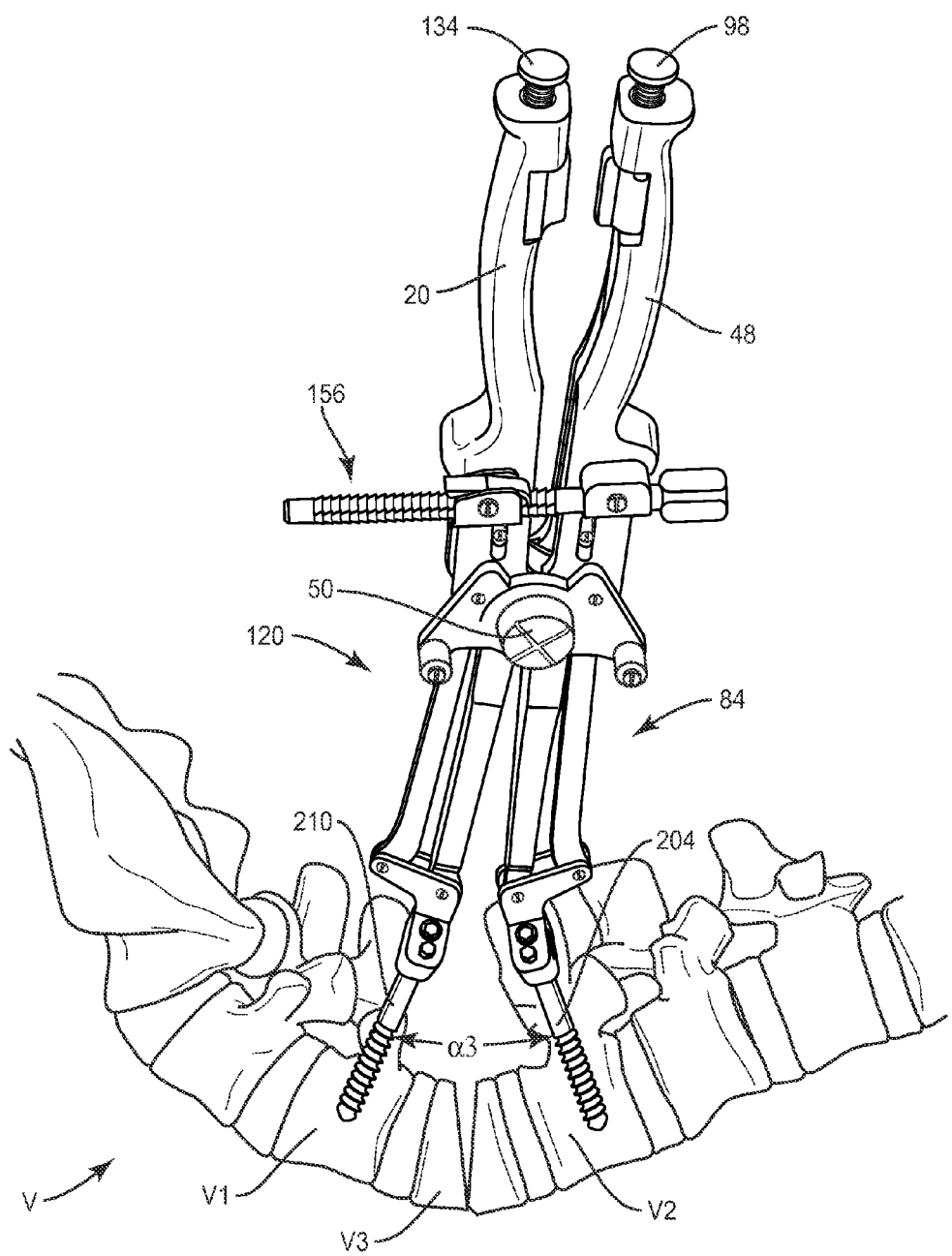
FIG. 5 is a perspective view of the system shown in FIG. 1 disposed with vertebrae.

To selectively adjust orientation of shaft 208 relative to pin 42 for penetration with vertebra V1, actuators 98, 134 cause linkages 84, 120, respectively, to orient fastener 204 relative to fastener 210 at an initial angle $\alpha 1$, as described above. The initial angle $\alpha 1$ is lockable via locks 100, 136, described above. Fasteners 204, 210 are rotatable to the second configuration, as shown in FIGS. 3 and 5, such that arms 20, 48 rotate fasteners 204, 210 for an angular correction of vertebrae V1, V2 in a sagittal plane of a body. Arms 20, 48 are drawn in adjacent relation and into close proximity, as shown by arrows I in FIG. 3, to rotate fastener 204 relative to fastener 210 through a closure angle $\alpha 2$ in the sagittal plane. Fastener 204 is rotated, in the direction shown by arrow J, relative to the pivot associated with pin 42. Fastener 204 is also rotated relative to a distal tip thereof disposed with vertebra V2 to facilitate angular correction. Fastener 210 is rotated, in the direction shown by arrow K, relative to the pivot associated with pin 78. Fastener 210 is also rotated relative to a distal tip thereof disposed with vertebra V1 to facilitate angular correction. Fasteners 204, 210 are disposed at a final angle $\alpha 3$, which includes angle $\alpha 1$ and angle $\alpha 2$. Final angle $\alpha 3$ is lockable via rack 156 described above.

In one embodiment, angles $\alpha 1$, $\alpha 2$, $\alpha 3$ are measured and displayed via the angle indicators and/or a spinal rod template may be disposed with a rod bender, as described above with regard to FIGS. 6 and 7. Upon completion of the procedure, instrument 12 is removed from the surgical site. It is contemplated that the non-implant components of system 10 are removed from the surgical site and the incision is closed.

It is contemplated one or a plurality of bone fasteners may be employed with a single vertebral level. It is further contemplated that the bone fasteners may be engaged with vertebrae in various orientations, such as, for example, series, parallel, offset, staggered and/or alternate vertebral levels. System 10 can be used with various bone fasteners, monoaxial screws, pedicle screws or multi-axial screws used in spinal surgery. System 10 may also include spinal rods, plates and connectors.

In one embodiment, system 10 includes an agent, which may be disposed, packed or layered within, on or about the components and/or surfaces of system 10. It is envisioned that the agent may include bone growth promoting material, such as, for example, bone graft to enhance fixation of the bone fasteners with vertebrae V. It is contemplated that the agent may include one or a plurality of therapeutic agents and/or pharmacological agents for release, including sustained release, to treat, for example, pain, inflammation and degeneration. The components of system 10 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of spinal implant system 10.

It is contemplated that the components of system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of system 10 and method of use may be used to prevent or minimize curve progression in individuals of various ages.

Figure 9:
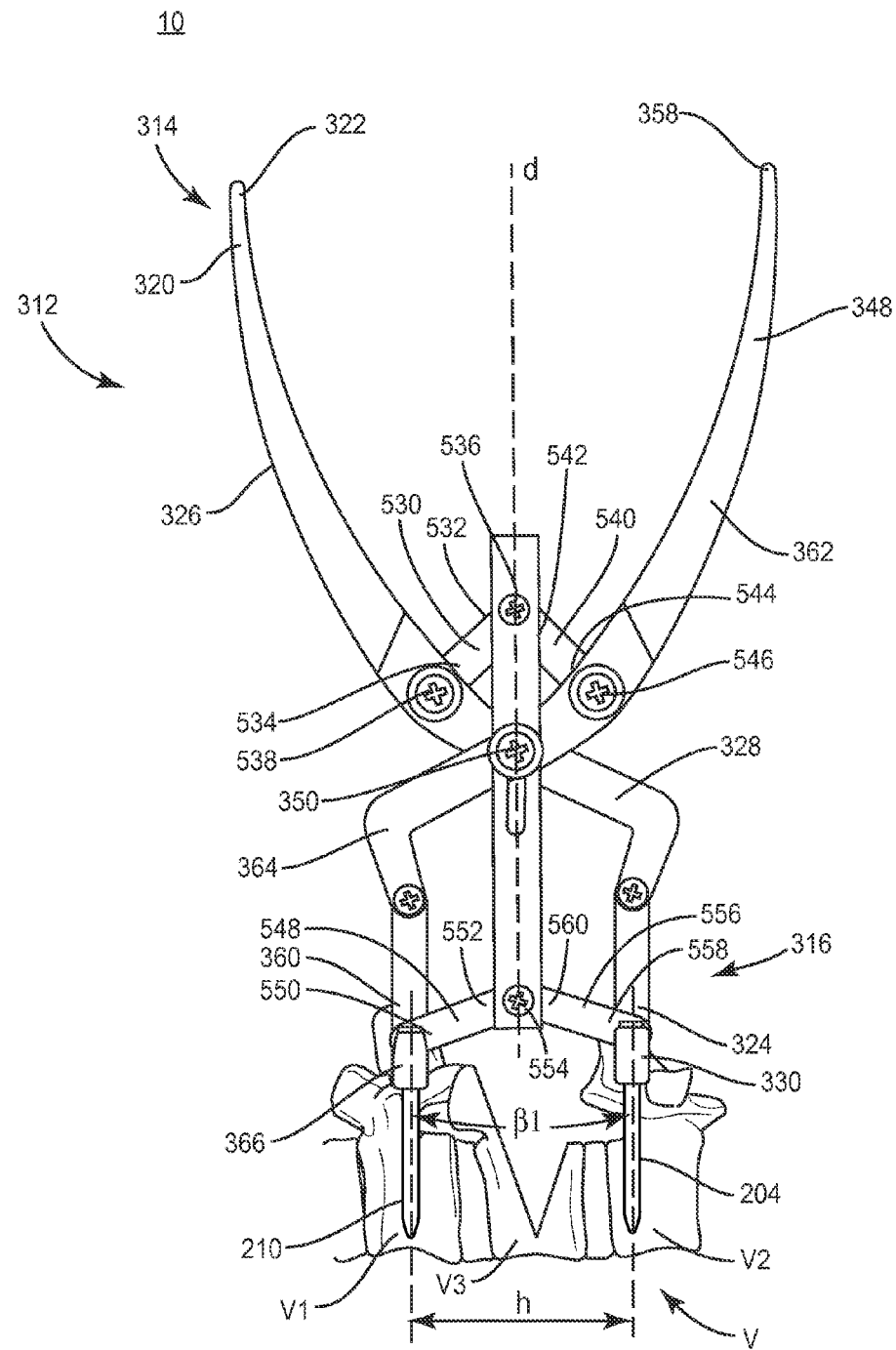
FIG. 9 is plan view of one embodiment of a spinal correction system in accordance with the principles of the present disclosure disposed with vertebrae.
Figure 10:
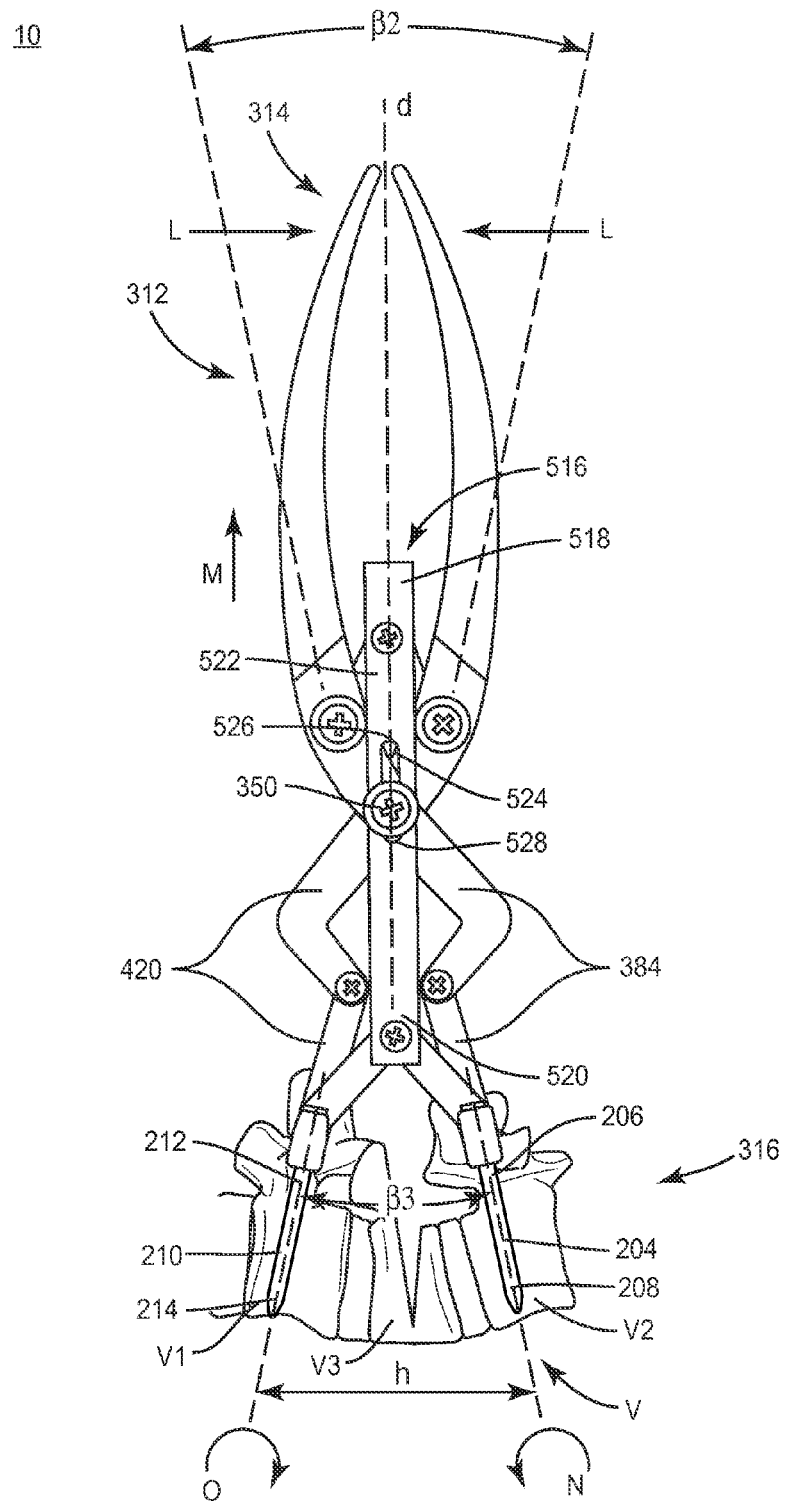
FIG. 10 is a plan view of the system and vertebrae shown in FIG. 9.

In one embodiment, as shown in FIGS. 9-10, system 10, similar to that described above with regard to FIGS. 1-8, comprises an instrument 312, similar to instrument 12 described above. Instrument 312 is configured for engagement with spinal constructs to angularly correct a sagittal deformity, as described herein. Instrument 312 extends between a first portion 314 and a second portion 316, and defines a longitudinal axis d.

Instrument 312 includes an arm 320 that extends between a first end 322 and a second end 324, and includes an arcuate configuration adjacent end 322. It is contemplated that the cross section and/or overall configuration of arm 320 may be variously configured, such as, for example, round, oval, oblong, square, rectangular, polygonal, irregular, uniform, non-uniform, offset, staggered, tapered, consistent or variable, depending on the requirements of a particular application. It is further contemplated that arm 320 may include an outer gripping surface configured for gripping by a hand of a practitioner. It is envisioned that the gripping surface may be, such as, for example, rough, undulating, mesh, porous, semi-porous, dimpled and/or textured according to the requirements of a particular application.

Arm 320 includes a member 326 disposed adjacent end 322 and a member 328 disposed adjacent end 324. Member 326 is integrally connected or monolithically formed with member 328 such that members 326, 328 simultaneously rotate relative to a second arm. Member 328 includes a pivot, such as, for example, an implant connector 330. Connector 330 is configured for engagement with a spinal construct disposed with a vertebral surface, as described herein. It is contemplated that connector 330 may be variously configured such as, for example, a screw, post and/or pin.

An arm 348 is connected to arm 320 via a pivot, such as, for example, hinge 350. Hinge 350 is centrally disposed with instrument 312 and configured to rotate arm 320 relative to arm 348 and relative to axis d. It is contemplated that hinge 350 may be variously configured such as, for example, those alternatives described herein. Arm 348 extends between a first end 358 and a second end 360. Arms 320, 348 are configured for engagement to move from a first configuration to a second configuration to angularly correct a sagittal deformity, as described herein. It is contemplated that the cross section and/or overall configuration of arm 348 may be variously configured, such as, for example, round, oval, oblong, square, rectangular, polygonal, irregular, uniform, non-uniform, offset, staggered, tapered, consistent or variable, depending on the requirements of a particular application. It is further contemplated that arm 348 may include an outer gripping surface configured for gripping by a hand of a practitioner. It is envisioned that the gripping surface may be, such as, for example, those alternative described herein.

Arm 348 includes a member 362 disposed adjacent end 358 and a member 364 disposed adjacent end 360. Member 362 is integrally connected or monolithically formed with member 364 such that members 362, 364 rotate relative to arm 320 and axis d. Member 364 includes a pivot, such as, for example, an implant connector 366. Connector 366 is configured for engagement with a spinal construct disposed with a vertebral surface, as described herein. It is contemplated that connector 366 may be variously configured such as, for example, those alternatives described herein.

Member 328 of arm 320 includes a linkage 384 configured for engagement with hinge 350 to rotate the vertebral construct, as described herein. Member 364 of arm 348 includes a linkage 420 configured for engagement with hinge 350 to rotate the vertebral construct, as described herein. Linkages 384, 420 are configured for engagement via an axial connector 516, as shown in FIG. 10. Connector 516 is axially translatable relative to hinge 350 for rotating linkages 384, 420 relative to connectors 330, 366. Connector 516 extends between a proximal portion 518 and a distal portion 520. An outer surface 522 defines an axial slot 524 that is configured for translation with hinge 350. Slot 524 includes a proximal limit 526 and a distal limit 528 that corresponds to a range of movement of arms 320, 348.

Connector 516 includes a bridge 530 that extends between a first portion 532 and a second portion 534. Portion 532 is configured for moveable fixation with portion 518 via a pin 536. Portion 534 is configured for engagement with a portion of member 326 of arm 320 via a pin 538. It is contemplated that the cross section and/or overall configuration of bridge 530 may be variously configured, such as, for example, round, oval, oblong, square, rectangular, polygonal, irregular, uniform, non-uniform, offset, staggered, tapered, consistent or variable, depending on the requirements of a particular application.

Connector 516 includes a bridge 540 that extends between a first portion 542 and a second portion 544. Portion 542 is configured for moveable fixation with portion 518 via pin 536. Portion 544 is configured for engagement with a portion of member 362 of arm 348 via a pin 546. It is contemplated that the cross section and/or overall configuration of bridge 540 may be variously configured according to the requirements of a particular application, such as, for example, those alternatives described herein.

Connector 516 includes a bridge 548 that extends between a first portion 550 and a second portion 552. Portion 550 is configured for engagement with connector 366 of arm 348. Portion 552 is configured for engagement with portion 520 via a pin 554. It is contemplated that the cross section and/or overall configuration of bridge 548 may be variously configured according to the requirements of a particular application, such as, for example, those alternatives described herein.

Connector 516 includes a bridge 556 that extends between a first portion 558 and a second portion 560. Portion 558 is configured for engagement with connector 330 of arm 320. Portion 560 is configured for engagement with portion 520 via pin 554. It is contemplated that the cross section and/or overall configuration of bridge 556 may be variously configured according to the requirements of a particular application, such as, for example, those alternatives described herein.

In assembly, operation and use, as shown in FIGS. 9-10, system 10 comprising instrument 312 is employed with a surgical procedure, similar to the systems and methods described above with regard to FIGS. 1-8. Instrument 312 is employed with a surgical correction treatment of an applicable condition or injury of an affected section of a spinal column and adjacent areas within a body, such as, for example, vertebrae V. A medical practitioner obtains access to a surgical site including vertebrae V1, V2, V3, similar to that described herein.

Pilot holes or the like are made in selected vertebra V1 and V2 of vertebrae V for receiving bone fasteners 204, 210. An instrument is disposed adjacent vertebrae V at a surgical site and is manipulated to drive, torque, insert or otherwise connect bone fasteners 204, 210 to vertebrae V1 and V2, according to the particular requirements of the surgical treatment. Vertebra V3 is osteotomised according to the particular procedure.

Instrument 312 is disposed adjacent the surgical site and manipulated for engagement with fasteners 204, 210 such that arms 320 and 348 are movable from a first configuration, as shown in FIG. 9. In the first configuration, arms 320, 348 are spaced apart and attached to bone fasteners 204, 210 such that hinge 350 is disposed at stop portion 526 of slot 524 of connector 516 and bone fastener 204 is disposed at a first angular orientation, such as, for example, angle β1 relative to bone fastener 210. Shaft 208 is fixed with vertebra V2 and shaft 214 is fixed with vertebra V1. In the first configuration, fasteners 204, 210 are spaced apart an anterior wall height h.

Fasteners 204, 210 are rotatable to the second configuration, as shown in FIG. 10, such that arms 320, 348 rotate fasteners 204, 210 for an angular correction of vertebrae V1, V2 in a sagittal plane of a body. Arms 320, 348 are drawn in adjacent relation and into close proximity, as shown by arrows L in FIG. 10, to rotate fastener 204 relative to fastener 210 through a closure angle β2 in the sagittal plane. Bridges 530, 540 are translated and drawn in an axial direction via pin 536, in the direction shown by arrow M, as hinge 350 axially translates in a relatively opposing direction and is disposed at stop portion 528 of slot 524.

During axial translation of hinge 350, bridges 548, 556 are translated via pin 554 and drawn in an axial direction, in the direction shown by arrow M. In the second configuration, bone fastener 204 is disposed at a second angular orientation, such as, for example, angle β3 relative to bone fastener 210. Fastener 204 is rotated, in the direction shown by arrow N, relative to connector 330. Fastener 204 is also rotated relative to a distal tip thereof disposed with vertebra V2 to facilitate angular correction. Fastener 210 is rotated, in the direction shown by arrow O, relative to connector 366. Fastener 210 is also rotated relative to a distal tip thereof disposed with vertebra V1 to facilitate angular correction.

Fasteners 204, 210 are disposed at a final angle β3, which includes angle β1 and angle β2. As fasteners 204, 210 are rotated and in the second configuration, height h is maintained substantially constant. Upon completion of the procedure, instrument 312 is removed from the surgical site. It is contemplated that the non-implant components of system 10 are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    a first arm extending between a first end and a second end including a first pivot that engages a first spinal construct configured to be disposed with a first vertebral surface; and
    a second arm connected with the first arm via a second pivot, the second arm extending between a first end and a second end including a third pivot that engages a second spinal construct configured to be disposed with a second vertebral surface such that the second spinal construct is spaced apart from the first spinal construct, wherein the arms are relatively movable to rotate the first spinal construct relative to the first pivot and the second spinal construct relative to the third pivot such that the first vertebral surface is moved relative to the second vertebral surface.

2. A surgical instrument as recited in claim 1, wherein the first arm includes a first member and a second member connected to the first member adjacent the second pivot, the second member including the first pivot.

3. A surgical instrument as recited in claim 2, wherein the second member includes a first linkage for rotating the first spinal construct.

4. A surgical instrument as recited in claim 3, wherein the first linkage comprises a parallelogram configuration for rotating the first spinal construct.

5. A surgical instrument as recited in claim 1, wherein the first arm includes a first member and a second member connected to the first member adjacent the second pivot, the second member including the first pivot, and the second arm including a first member and a second member connected to the first member of the second arm adjacent the second pivot, the second member of the second arm including the third pivot.

6. A surgical instrument as recited in claim 5, wherein the second member of the first arm includes a first linkage for rotating the first spinal construct and the second member of the second arm includes a second linkage for rotating the second spinal construct.

7. A surgical instrument as recited in claim 6, wherein the first arm includes a first actuator connected to the second linkage, the first actuator being configured to selectively adjust rotation of the second spinal construct.

8. A surgical instrument as recited in claim 6, wherein the first arm includes a first actuator connected to the second linkage, the first actuator being configured to selectively adjust rotation of the second spinal construct, and the second arm includes a second actuator connected to the first linkage, the second actuator being configured to selectively adjust rotation of the first spinal construct.

9. A surgical instrument as recited in claim 1, wherein the arms are connected via a transverse connector, the transverse connector being configured to facilitate relative movement of the arms.

10. A surgical instrument as recited in claim 1, wherein the second pivot includes visual indicia of an angular orientation of the first spinal construct relative to the second spinal construct.

11. A surgical instrument as recited in claim 10, wherein the visual indicia includes numerical graduations.

12. A surgical instrument as recited in claim 1, wherein the arms are selectively movable from a first configuration such that the first spinal construct is disposed at a first angular orientation relative to the second spinal construct and a second configuration such that the first spinal construct is disposed at a second angular orientation relative to the second spinal construct.

13. A surgical instrument as recited in claim 1, wherein the first pivot selectively rotates the first spinal construct and the third pivot selectively rotates the second spinal construct such the first spinal construct is disposed at a first angular orientation relative to the second spinal construct in a first configuration and the arms are selectively movable from the first configuration to a second configuration such that the first spinal construct is disposed at a second angular orientation relative to the second spinal construct.

14. A surgical instrument as recited in claim 1, wherein the first spinal construct includes a bone fastener extending between a posterior end and an anterior end, wherein the posterior end is fixed with the first pivot and the anterior end rotates relative to the first pivot.

15. A surgical instrument as recited in claim 1, wherein the spinal constructs and the vertebral surfaces are rotated in a sagittal plane of a body.

16. A surgical instrument as recited in claim 1, wherein the second pivot includes a spinal rod bender.

17. A surgical instrument comprising:
    a first arm including a first member and a second member connected to the first member adjacent a first pivot, the second member including a second pivot that engages a first bone fastener that extends between a posterior end and an anterior end configured for disposal with a first vertebral surface, the second member further including a first linkage connected with the second pivot; and
    a second arm including a first member and a second member connected to the first member of the second arm adjacent the first pivot, the second member of the second arm including a third pivot that engages a second bone fastener such that the second bone fastener is spaced apart from the first bone fastener, extends the second bone fastener extending between a posterior end and an anterior end configured for disposal with a second vertebral surface that is spaced apart a distance from the first vertebral surface, the second member of the second arm further including a second linkage connected with the third pivot, wherein the first linkage engages the second pivot to selectively and relatively rotate the first bone fastener and the second linkage engages the third pivot to selectively and relatively rotate the second bone fastener such the first bone fastener is disposed at a first angular orientation relative to the second bone fastener in a first configuration and the arms are selectively movable from the first configuration to a second configuration to rotate the bone fasteners relative to the pivots such that the first bone fastener is disposed at a second angular orientation relative to the second bone fastener.

18. A surgical instrument as recited in claim 17, wherein the first pivot includes visual indicia of an angular orientation of the first bone fastener relative to the second bone fastener.

19. A method for treating a spine, the method comprising the steps of:

providing a surgical instrument including a first arm extending between a first end and a second end including a first pivot and a second arm connected with the first arm via a second pivot, the second arm extending between a first end and a second end including a third pivot;

providing a first spinal construct disposed with a first vertebral surface of a body;

providing a second spinal construct disposed with a second vertebral surface of the body that is spaced apart from the first vertebral surface;

connecting the first pivot with the first spinal construct and the third pivot with the second spinal construct; and moving the first arm relative to the second arm to rotate the first spinal construct relative to the first pivot and the second spinal construct relative to the third pivot such that the spinal constructs and the vertebral surfaces are rotated in a sagittal plane of the body.

20. A method as recited in claim 19, wherein the step of moving includes the first pivot selectively rotating the first spinal construct and the third pivot selectively rotating the second spinal construct such the first spinal construct is disposed at a first angular orientation relative to the second spinal construct in a first configuration and the arms are selectively movable from the first configuration to a second configuration such that the first spinal construct is disposed at a second angular orientation relative to the second spinal construct.

* * * * *